(12) United States Patent
Dower et al.

(10) Patent No.: US 8,828,020 B2
(45) Date of Patent: Sep. 9, 2014

(54) FEMORAL SIZING INSTRUMENT (75) Inventors: Liam Dower, Haddenham (GB); Mark Heldreth, Warsaw, IN (US); Mark Pagnano, Rochester, MN (US)

(73) Assignee: DePuy (Ireland), Cork (IE)

( * ) Notice: Subject to any disclaimer, the term of this patent is extended or adjusted under 35 U.S.C. 154(b) by 311 days.

(21) Appl. No.: 13/376,852

(22) PCT Filed: Jun. 7, 2010

(86) PCT No.: PCT/GB2010/050953
§ 371 (c)(1),
(2), (4) Date: Feb. 22, 2012

(87) PCT Pub. No.: WO2010/142980
PCT Pub. Date: Dec. 16, 2010

(65) Prior Publication Data
US 2012/0143205 A1    Jun. 7, 2012

(30) Foreign Application Priority Data

Jun. 9, 2009   (GB) .................................. 0909918.5

(51) Int. Cl.
| | |
|---|---|
| *A61B 17/58* | (2006.01) |
| *A61B 17/60* | (2006.01) |
| *A61F 2/00* | (2006.01) |
| *A61B 5/107* | (2006.01) |
| *A61F 2/46* | (2006.01) |
| *A61B 19/00* | (2006.01) |
| *A61B 5/00* | (2006.01) |
| *A61F 2/38* | (2006.01) |

(52) U.S. Cl.
CPC .......... *A61B 5/1072* (2013.01); *A61B 2019/461* (2013.01); *A61F 2/4657* (2013.01); *A61B 5/4528* (2013.01); *A61F 2002/4658* (2013.01); *A61B 5/6878* (2013.01); *A61F 2/3859* (2013.01)

USPC .............................................. 606/102; 606/88

(58) Field of Classification Search
CPC ................ A61F 2/4657; A61F 2/4684; A61F 2002/4658; A61B 19/46; A61B 2019/461
USPC .................................... 606/102, 88, 86 R, 87
See application file for complete search history.

(56) References Cited

U.S. PATENT DOCUMENTS 6,056,756 A *  5/2000  Eng et al. ......................... 606/87
6,458,135 B1  10/2002  Harwin
(Continued)

FOREIGN PATENT DOCUMENTS

WO   WO 9721390 A1   6/1997
WO   WO 2007007067 A2   1/2007

OTHER PUBLICATIONS

PCT International Application No. PCT/GB2010/050953 Search Report and Written Opinion dated Sep. 23, 2010.

(Continued)

*Primary Examiner* — David Bates
*Assistant Examiner* — Samuel Hanna (57) ABSTRACT

A femoral sizing instrument for use in a knee joint replacement procedure has a housing which includes formations (4) by which it can be located relative to the femoral posterior condyles. A cortex arm (14) has a tip (16) for engaging the anterior cortex of the femur and a sulcus arm (20) has a tip (24) for engaging the sulcus. Each of the cortex and sulcus arms can be adjusted relative to the housing to adjust the distance between its tip and the posterior condyles measured generally parallel to the anterior posterior axis. The instrument includes at least one scale (13,23,27,25) for indicating the positions of the tips of the cortex and sulcus arms relative to the posterior condyles.

8 Claims, 4 Drawing Sheets

(56) References Cited

U.S. PATENT DOCUMENTS

2004/0215205 A1  10/2004  Plumet
2004/0220583 A1  11/2004  Pieczynski
2005/0187560 A1  8/2005  Dietzel
2007/0173851 A1  7/2007  McMillen

OTHER PUBLICATIONS

GB Application No. 0909918.5 Search Report—Search date Sep. 29, 2009.

* cited by examiner

FEMORAL SIZING INSTRUMENT

CROSS REFERENCE TO RELATED APPLICATION

This application is a National Stage 35 U.S.C. 371 of International Patent Application PCT/GB2010/050953 filed Jun. 7, 2010.

BACKGROUND OF THE INVENTION

This invention relates to a femoral sizing instrument for use in a knee joint replacement procedure.

Femoral components of knee joint prostheses are generally available in several sizes to accommodate variations in bone size and shapes between patients. Preparing the distal femur to receive the femoral component of a knee joint prosthesis involves resecting the bone so that it is appropriately shaped to ensure that the femoral component is an appropriately close fit. Commonly used surgical techniques involve making distal, anterior, posterior, anterior chamfer and posterior chamfer cuts. The locations of the cuts are determined according to the size of the selected implant.

It is common to choose the size of the femoral component with reference to the measured distance along the anterior posterior axis between the posterior condyle and the anterior cortex. This can enable a close fit between the anterior flange of the femoral component and the anterior cortex.

BRIEF SUMMARY OF THE INVENTION

The present invention provides an instrument which can be used to choose the size of a femoral component with reference to the measured distance between the anterior and posterior condyles.

In one aspect, the invention provides a femoral sizing instrument for use in a knee joint replacement procedure, which comprises:
  a. a housing which includes formations by which it can be located relative to the femoral posterior condyles,
  b. a cortex arm having a tip for engaging the anterior cortex of the femur,
  c. a sulcus arm having a tip for engaging the sulcus,
in which each of the cortex and sulcus arms can be adjusted relative to the housing to adjust the distance between its tip and the posterior condyles measured generally parallel to the anterior posterior axis, and
  d. at least one scale for indicating the positions of the tips of the cortex and sulcus arms relative to the posterior condyles.

The instrument of the invention has the advantage that it enables the size of a patient's femur, measured between the anterior and posterior condyles, to be taken into account when selecting an appropriate size of femoral component of a knee joint prosthesis. These data can be taken into account together with data from the measurement of the distance between the posterior condyles and the anterior cortex. Factors which can affect the choice of the size of the femoral component include:
  The femoral component should be sufficiently large to avoid the need to create a notch in the anterior cortex at the proximal edge of the component. Such a notch can be a point of weakness in the bone after implantation of the prosthesis.
  The femoral component should not be so large that it leads to an undesirable discontinuity between the anterior flange of the component at its proximal edge between it and the anterior cortex.
  The femoral component should be sufficiently large that soft tissue connected to the patella is maintained under sufficient tension during flexion to ensure that the joint between the patella and the implanted femoral component is stable.
  The femoral component should not be so large that tension on soft tissue connected to the patella restricts flexion.

These fitting requirements can be addressed alternatively by appropriate adjustment of the position of the femoral component along the anterior posterior axis to suit a patient in whose knee the sulcus depth which is greater or less than would be suitable to accommodate a particular femoral implant component. It can be seen accordingly that the measurement techniques that are provided by the present invention enable selection of either or both of implant size and implant position to be optimised.

The cortex arm can be used to measure the patient's femur along the anterior posterior axis, between the posterior condyles and the anterior cortex. This measurement can be performed by placing the housing appropriately relative to the femoral posterior condyles, and moving the cortex arm until its tip is in contact with the anterior cortex. As is known, for example in the instrument system which is sold by DePuy Orthopaedics Inc under the trade mark Sigma High Performance Classic, a scale can be included which can provide a surgeon with an indication of the appropriate size of femoral component which should be used. The appropriate size of femoral component can help to minimise any discontinuity between the anterior flange of the component at its proximal edge between it and the anterior cortex, while also minimising the need to create a notch in the anterior cortex at the proximal edge of the component. Such a notch can be a point of weakness in the bone after implantation of the prosthesis.

The sulcus arm can be used to measure the patient's femur along the anterior posterior axis, between the posterior condyles and the sulcus (being the shallow valley between the anterior condyles). This measurement can be performed by placing the housing appropriately relative to the femoral posterior condyles, and moving the sulcus arm until its tip is in contact with the sulcus. The measurement will generally be taken at the point along the valley between the anterior condyles at which the distance from the posterior condyle to the valley (measured parallel to the anterior/posterior axis) is at a maximum. Information from this measurement can indicate to the surgeon the appropriate size of femoral component which should be used so that soft tissue connected to the patella is maintained under sufficient tension during flexion to ensure that the joint between the patella and the implanted femoral component is stable, but not so large that tension on soft tissue connected to the patella restricts flexion.

The cortex and sulcus arms should be capable of movement relative to the posterior condyles so that they can provide independent measurement data for the two measurements (between the posterior condyles and the anterior cortex and the sulcus respectively). A first one of the cortex and sulcus arms can be mounted on the housing so that the height of the said first arm along the anterior posterior axis relative to the housing can be adjusted. The second one of the cortex and sulcus arms can be mounted on the first arm so that the height of the said second arm along the anterior posterior axis relative to the housing can be adjusted. For example, the cortex arm can be mounted on the housing so that its height relative to the housing can be adjusted. The sulcus arm can be mounted on the cortex arm so that it moves relative to the housing with the cortex arm. The sulcus arm can be moved relative to the cortex arm. In use, the housing is located relative to the posterior condyles and the anterior arm is moved until its tip is in contact with the anterior cortex. The sulcus arm is then moved relative to the cortex arm until its tip is in contact with the sulcus.

Alternatively, the sulcus arm can be mounted on the housing so that its height relative to the housing can be adjusted. The cortex arm can be mounted on the sulcus arm so that it moves relative to the housing with the sulcus arm. The cortex arm can be moved relative to the sulcus arm. In use, the housing is located relative to the posterior condyles and the sulcus arm is moved until its tip is in contact with the sulcus. The cortex arm is then moved relative to the sulcus arm until its tip is in contact with the anterior cortex.

When a first one of the cortex and sulcus arms is mounted on the second one of the cortex and sulcus arms, so that the first arm can slide along the second arm, the nature of the engagement between the first and second arms can be such that the path which is defined for the second arm to slide along is not parallel to the axis of the bone (when the bone is viewed from one side along the lateral-medial axis). For example, the second arm might define a ramp for the first arm to slide along. The ramp surface might be inclined so that the first arm is displaced in an anterior direction away from the bone axis as it is slid along the second arm in a superior to inferior direction. The ramp surface might be inclined so that the first arm is displaced in a posterior direction towards the bone axis as the arm is slid along the second arm in an inferior to superior direction. The ramp might arise as a result of the second arm being formed with an appropriate shape. For example, the ramp might arise as a result of a variation in the thickness of the material of the second arm, or by bending an arm made with a constant thickness.

The selection of a ramp shape can be selected according to known variations across the relevant population in the distance from the posterior condyle to the sulcus relative to the distance from the posterior condyle to the anterior cortex, and the corresponding distances across a range of femoral components which are designed to accommodate those variations across the population. The ramp will frequently have an approximately constant inclination along its length. The ratio of the anterior/posterior height to the inferior/superior length will generally be not more than about 1.0, preferably not more than about 0.9, for example about 0.8. The said ratio will generally be at least about 0.5, preferably at least about 0.6.

For example, in an embodiment of an instrument according to the invention, the sulcus arm can be mounted on the cortex arm so that the sulcus arm can slide along the cortex arm. The surface of the cortex arm which faces away from the bone, against which the sulcus arm acts, can be inclined to the bone axis so that the distance between that surface and the axis increases in the superior to inferior direction. This can be achieved by increasing the thickness of the cortex arm. Alternatively, the distance between the surface of the cortex arm and the bone axis might decrease in the inferior to superior direction. Furthermore, the movement of a first arm along a second arm might be in a direction which is approximately parallel to the bone axis when the viewed is viewed from one side along the lateral-medial axis.

The relationship between the path followed by one of the arms relative to the bone axis (as discussed above) can be determined to take account of the configuration of the implant component with which the instrument is to be used and the variation in dimensions of the implant component between sizes. In particular, a ramp can give rise to advantages when the thickness of the superior portion of a femoral component varies between different sizes of the component.

The instrument can include a first scale for indicating the distance between the tip of the cortex arm and the posterior condyles, and a second scale for indicating the distance between the tip of the sulcus arm and the posterior condyles. The instrument can include a first scale for indicating the distance between the tip of a first one of the cortex and sulcus arms and the posterior condyles, and a second scale for indicating the distance between the tips of the sulcus and condyle arms. The distance between the tip of the second one of the cortex and sulcus arms and the posterior condyles can be derived from the second scale. Use of a second scale for indicating the distance between the tips of the sulcus and condyle arms will generally involve making an initial assessment of the appropriate size of a femoral implant component based on the measured distance between the tip of one of the arms and the posterior condyles, with the measurement of the distance between the tips of the two arms being used to assess whether a variation in the initial assessment is required. For example, a first scale can be used to indicate the distance between the posterior condyles and the anterior cortex. A second scale can be used to determine whether the distance between the anterior cortex and the sulcus is such that a variation on the size of implant which is determined using the first scale is appropriate in order to ensure appropriate tension in soft tissue associated with the patello-femoral joint.

The scale which is provided to indicate a measurement can provide information concerning the absolute distance from the posterior condyles to the anterior cortex or to the sulcus as the case may be. It will however frequently be preferred for the scale to provide information directly concerning the size of the femoral component of a knee joint prosthesis which is suitable according to the measured distance.

When a scale is provided to provide information concerning distance between the tips of the sulcus and condyle arms, it can provide information concerning the absolute distance between the tips. It will however frequently be preferred for the scale to provide information concerning the variation from the statistically derived expected distance, which might cause a surgeon to vary the size of the femoral component which is to be implanted. For example, the scale might indicate that the size of femoral component should be reduced by one size, or that it should be increased by one size. For example, one of the sulcus and condyle arms might provide an indication of the implant size, and the other of the arms might provide an indication that the size should be increased or decreased by one size.

The arm or each arm which is mounted on the housing should preferably be capable of adjustment so that the distance between the posterior condyles and the tip of the arm, measured generally parallel to the anterior posterior axis, can be adjusted, and also so that the effective length of the arm, measured between the housing and the tip measured generally along the axis of the bone, can be adjusted.

Preferably, the cortex arm is capable of adjustment so that the distance between the posterior condyles and its tip, measured generally parallel to the anterior posterior axis, can be varied through at least about 40 mm. Preferably, the distance will be variable through not more than about 75 mm.

Preferably, the sulcus arm is capable of adjustment so that the distance between the posterior condyles and its tip, measured generally parallel to the anterior posterior axis, can be varied through at least about 40 mm. Preferably, the distance will be variable through not more than about 80 mm.

Preferably, the cortex and sulcus arms are capable of adjustment so that the distance between their tips, measured generally parallel to the anterior posterior axis, can be varied through at least about 5 mm. Preferably, the distance will be variable through not more than about 15 mm.

Preferably, the effective length of the cortex arm along the superior inferior axis measured between the housing and the tip of the cortex arm can be adjusted. Preferably, the effective length of the sulcus arm along the superior inferior axis measured between the housing and the tip of the sulcus arm can be adjusted.

It can be preferred that the first one of the cortex and sulcus arms defines a track for the second one of the cortex and sulcus arms to slide along to adjust the distance between the tips of the cortex and sulcus arms, measured along the superior inferior axis, and in which the instrument includes a locking feature to lock the second one of the cortex and sulcus arms against movement along the track. For example, one of the arms can have a slot formed in it, and the other arm can have a spigot which extends through the slot, and which can slide along the slot. Such a spigot can be threaded at its free end, to receive a nut which can clamp against a top face of the slot to provide the lock. Other track arrangements can be envisaged, for example in which the second arm has a groove formed in it at one end, which can receive the first arm.

It can be preferred for the housing to have a first location face which can be located relative to the distal face of the femur, and a second location face which can be located relative to a posterior condyle. This combination of first and second location faces can be used to locate the housing relative to the posterior condyles of the femur while performing the anterior posterior measurements using the instrument. As is commonly the case with existing instruments, the measurements of the anterior posterior dimension of the femur will generally be performed with the instrument of the invention after an initial distal resection. One example of a technique for determining the appropriate location and orientation of the distal resection plane uses the plane on which the tibia has been resected as a point of reference. The first location face of the housing component of the instrument of the invention can then be placed in contact with the resected distal surface of the femur.

Preferably, the housing includes a connector leg which extends between the housing and one of the cortex and sulcus arms and is movable relative to the housing so that the length of the connector leg, measured from the housing to the said one of the cortex and sulcus arms, can be adjusted. This can provide for adjustment of the distance measured generally parallel to the anterior posterior axis between the posterior condyles and the tip of one or each of the arms. The instrument can include a leg locking device by which the position of the connector leg relative to the housing can be locked.

In some constructions, the extension of the connector leg relative to the housing might be described as telescopic.

The connector leg can be received in a slot in the housing, in which it can slide. The connector leg might have a groove formed in it, in which a rib on the housing can be received. The connector leg and the housing can provide a scale which indicates the extent of the extension of the connector leg relative to the housing, and therefore of the distance measured generally along the anterior posterior axis from the posterior condyles to the tip of the arm which is connected to the housing by the connector leg. This distance can be related to the size of the appropriate implant which should be used according to the size of the patient's femur.

Preferably, the cortex arm or the sulcus arm which is connected to the housing by means of the connector leg can slide relative to the connector leg. This can provide for adjustment of the effective length of the arm, measured between the housing and the tip of the arm. The instrument can include an arm locking device to lock the arm against sliding relative to the connector leg. Locking devices which can be used to lock an arm against sliding relative to a connector leg are known in existing measurement devices such as the measuring device in the instrument system which is sold by DePuy Orthopaedics Inc under the trade mark Sigma High Performance Classic. A suitable locking device can include a threaded nut.

The housing can include formations such as hollow bores by which it can be fastened to a femur, for example using pins or screws, if required by a surgeon.

In another aspect, the invention provides a method of measuring the distal femur in a knee replacement procedure using an instrument according to the invention, which comprises:
 a. locating the housing relative to the femoral posterior condyles,
 b. moving a first one of the sulcus and cortex arms so that its tip is in contact with the sulcus or the anterior cortex respectively,
 c. deriving information as to the size of the femur from the position of the tip of the first one of the sulcus and cortex arms relative to the femoral posterior condyles to identify an implant component provisionally,
 d. moving a second one of the sulcus and cortex arms so that its tip is in contact with the sulcus or the anterior cortex respectively,
 e. assessing based on information as to the distance between the tip of the second one of the sulcus and cortex arms relative to the femoral posterior condyles whether to vary the size and or the anterior/posterior position of the implant component identified in step (c).

The instrument of the invention can be made from materials which are conventionally used in the manufacture. These frequently include metals such as certain stainless steels. Polymeric materials can be used for all or part of the instrument.

The instrument of the invention can be used to determine the size of the femur for the purpose of implanting a femoral component of a whole knee joint prosthesis.

The instrument of the invention can be used to determine the size of the femur for the purpose of implanting a femoral component of a partial knee joint prosthesis, for example in which just one compartment of the joint is replaced (which might be the medial compartment or the lateral compartment).

The instrument of the invention can be used to determine the size of the femur for the purpose of implanting a partial femoral component, for example in which the component is a patellofemoral component which can be fitted to the anterior face of the femur.

BRIEF DESCRIPTION OF THE DRAWINGS

Embodiments of the invention will now be described by way of example with reference to the accompanying drawings, in which.

DETAILED DESCRIPTION OF THE INVENTION

Figure 1:
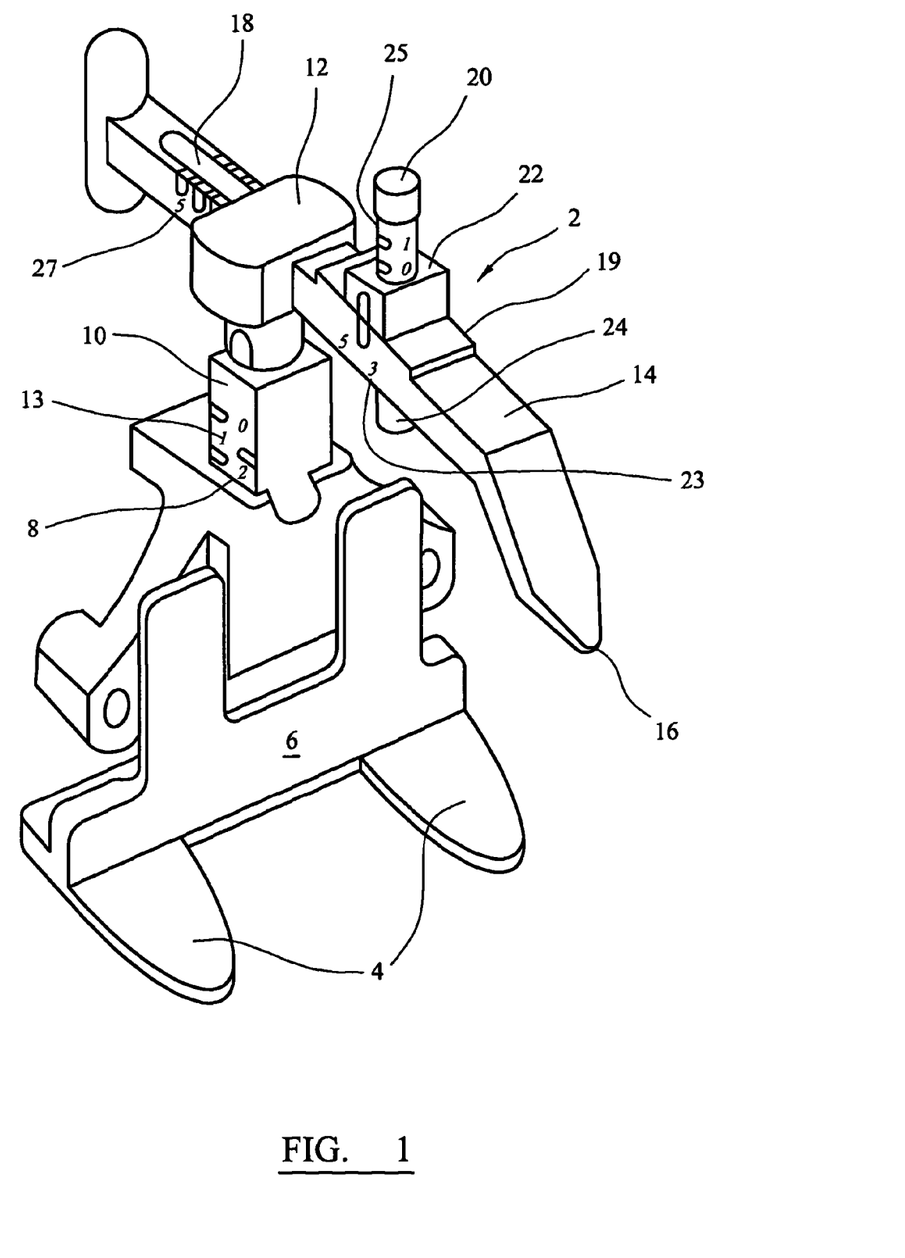
FIG. 1 is an isometric view of a femoral sizing instrument for use in a knee joint replacement procedure.

Referring to the drawings, FIG. 1 shows an instrument 2 for measuring a femur in a knee joint replacement procedure. It comprises a housing with posterior plates 4 and a distal plate 6. The housing has a bore 8 formed in it in which a connector leg 10 can be received and can slide, in a direction which is generally parallel to the distal plate 6. The position of the connector leg can be clamped against sliding relative to the housing by means of a threaded screw which can be screwed into a threaded hole in the housing so that the end of the screw acts against the connector leg. Locking screws of this type are known.

The connector leg has a hub 12 its upper end with a bore extending through it. The connector leg has a scale 13 marked on it.

The instrument includes an anterior arm 14. The anterior arm is sized to be a sliding fit in the bore in the hub 12 on the connector leg. The anterior arm 14 has a tip 16. It has a slot 18 formed in it extending along part of its length. The thickness of the anterior arm increases along the length of the slot, towards the tip of the arm so that the anterior face 19 of the arm defines an inclined ramp surface.

The instrument includes a sulcus arm 20. The sulcus arm is mounted in a plate 22 which fits on to the anterior arm and can be slid along the slot 18 therein. The anterior arm has first a scale 23 on one side to indicate the position of the sulcus arm 20 and of its plate 22 along the length of the slot. It has a second scale 27 on it to indicate the position of the anterior arm relative to the hub 12 on the connector leg.

The sulcus arm can slide within the plate 22. The sulcus arm has a tip 24. The sulcus arm has a scale 25 on one side to indicate the position of the sulcus arm within the plate.

Figure 2:
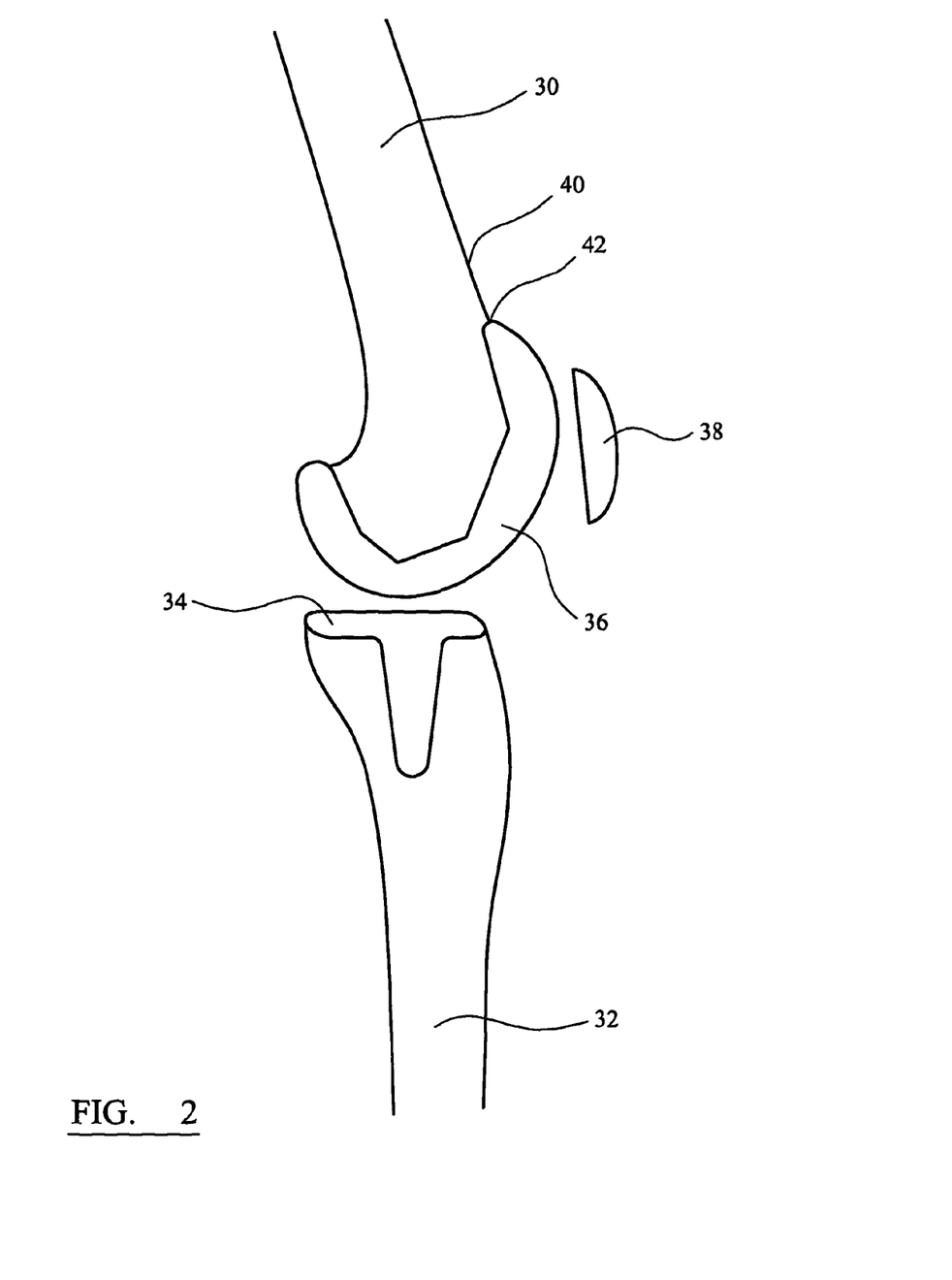
FIG. 2 is a view along the medial lateral axis of a knee joint after implantation of a knee joint prosthesis.

FIG. 2 shows a knee joint between a femur 30 and a tibia 32. A tibial component 34 of a knee joint prosthesis has been implanted in the tibia. A femoral component 36 has been implanted in the femur. The patella 38 articulates against the femoral component during flexing of the joint.

The present invention is concerned with determining the size of the femur so that an appropriately sized femoral component 36 of the knee joint prosthesis is selected for implantation. The component should be sufficiently large to avoid the need to create a notch in the anterior cortex 40 at the proximal edge 42 of the component. Such a notch can be a point of weakness in the bone after implantation of the prosthesis. However, the component should not be so large that it leads to an undesirable discontinuity between the anterior flange of the component at its proximal edge 42 between it and the anterior cortex 40. This is determined with reference to the distance measured parallel to the anterior posterior axis between the posterior condyles and the anterior cortex in the patient's natural knee (as described below with reference to FIG. 3)

The femoral component 36 should be sufficiently large that soft tissue connected to the patella 38 is maintained under sufficient tension during flexion to ensure that the joint between the patella and the implanted femoral component is stable. However, the component should not be so large that tension on soft tissue connected to the patella restricts flexion. This is determined with reference to the distance measured parallel to the anterior posterior axis between the posterior condyles and the sulcus in the patient's natural knee (as described below with reference to FIG. 3)

Figure 3:
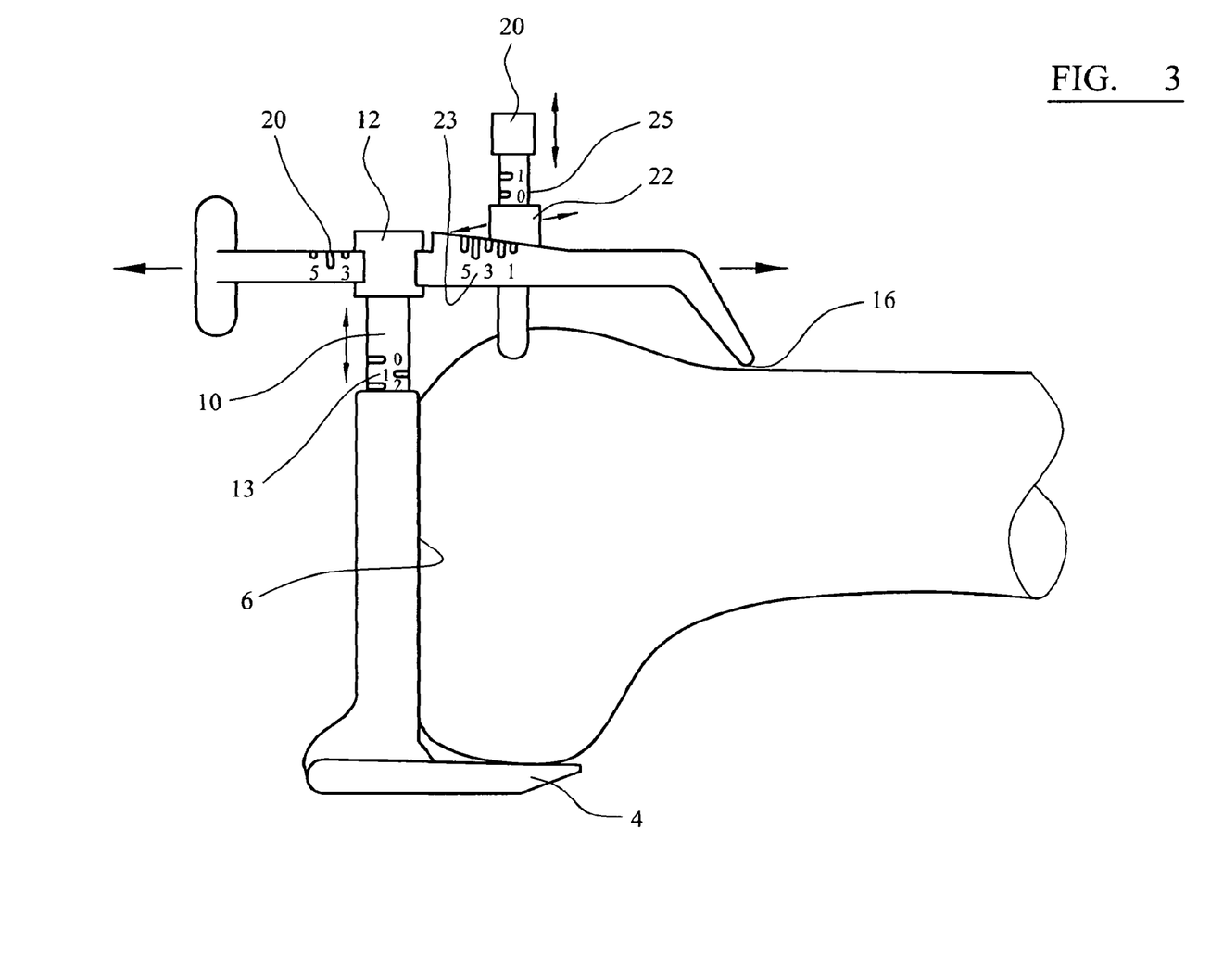
FIG. 3 is a view along the medial lateral axis of the instrument shown in FIG. 1, in position relative to the distal end of a patient's femur.

FIG. 3 shows the instrument of the invention positioned against a patient's femur during preparation of the femur to receive the femoral component of a knee joint prosthesis. As shown in FIG. 3, the femur has been resected distally to create a planar distal face 30. The position and orientation of the distal resection plane can be determined using conventional techniques.

The size of the femur is determined for the purpose of selecting an appropriately sized femoral component. A first measurement which is made conventionally between the patient's posterior condyles 50 and the anterior cortex 52, measured parallel to the anterior posterior axis 54. This is to minimise the risks of (a) having to create a notch in the anterior cortex at the proximal edge of the selected femoral component, and (b) an undesirable discontinuity between the anterior flange of the component at its proximal edge between it and the anterior cortex.

A second measurement is between the patient's posterior condyles 50 and the sulcus (that is, the shallow valley between the anterior condyles), measured parallel to the anterior posterior axis 54. This is to minimise the risk of soft tissue connected to the patella being in appropriately tensioned so that the patello-femoral joint is not stable or so that flexing of the knee joint after joint replacement is unduly restricted.

Accordingly, in a first measurement step, the instrument of the invention is placed with the distal plate 6 in contact with the resected distal face of the femur and the posterior plates 4 in contact with the posterior condyles 50. The connector leg 10 is slid out of the bore 8 in the housing sufficiently to allow the anterior arm 14 to be moved parallel to the superior inferior axis of the femur. The anterior arm is then moved until its tip 16 is positioned beyond the interface 56 between the anterior condyles and the anterior cortex (which is the point to which the anterior flange of the femoral component of the knee joint prosthesis will extend once implanted). The connector leg is then slid into the bore 8 in the housing until the tip of the anterior arm contacts the femur. Throughout this manipulation of the anterior arm 14, the sulcus arm 20 is maintained in a retracted position relative to the plate 22 so that its tip 24 is spaced apart from the anterior face of the femur.

The scale 13 on the connector leg provides a first indication of the size of the patient's femur. This provides a point of reference for subsequent measurement steps. The scale can provide an indication of the absolute distance (for example in millimeters) between the posterior condyles and the anterior cortex, measured generally parallel to the anterior posterior axis. Alternatively, it can be preferred for the scale to provide directly an indication of the size of a femoral component which is suitable for the size of the measured femur (for example ranging in integers from 1 to 7).

Accordingly, the first size indication from the scale 13 on the connector leg is used to set the position of the anterior arm 14 relative to the hub 12, using the scale 27 on the arm.

The second measurement step is performed once the tip 16 of the anterior arm 14 has been positioned in contact with the anterior cortex. The sulcus arm 20 with its plate 22 is moved along the anterior arm 14 in the slot 18, and positioned relative to the anterior arm using the first indication which is derived from the scale 13 on the connector leg (as described above). This movement will be along the ramp surface. The sulcus arm is then lowered through the plate until its tip 24 is contact with the sulcus, measured at the point along the valley between the anterior condyles at which the distance from the posterior condyle to the valley (measured parallel to the anterior/posterior axis) is at a maximum.

It will be noted that the position of the anterior arm relative to the hub (indicated by scale 27 on the anterior arm to indicate the position of the arm relative to the hub), and the position of the sulcus arm within the slot in the anterior arm (indicated by the scale 23 on the anterior arm for the sulcus arm), are both set with reference to the first size indication from the scale 13. The markings on the hub scale 27 are derived from the distance from the distal condyle to the anterior flange across the range of sizes of the femoral implant component. The markings on the sulcus arm scale 23 are derived from the maximum thickness of the anterior flange across the range of sizes of the femoral implant component. Accordingly, the distance between the size markings on the hub scale 27 is greater than the distance between the markings on the sulcus arm scale 23. For example, in a preferred embodiment, the distance between the markings on the hub scale 27 between the smallest and largest sizes of implant in a size range might be 15 mm and the distance between the markings on the sulcus arm scale 23 between the largest and smallest sizes of implant in that size range might be 5 mm.

The scale 25 on the sulcus arm 20 can provide directly an indication of the suitability of the size of the femoral component as determined in the first measurement step, having regard to the measured distance between the posterior condyles and the sulcus. Accordingly, the scale 25 might provide a set of readings ranging from "−2", through "0", to "+2". On this scale, a reading of "0" from the measurement of the posterior condyle to sulcus distance would indicate that the size of the femoral component derived from the first size measurement is appropriate to maintain appropriate soft tissue tension in the patello-femoral joint. A reading which is less than "0" would indicate that a smaller size of femoral component should be selected in order to avoid a restriction on joint flexion as a result of soft tissue in the patello-femoral joint being too tight. A reading which is greater than "0" would indicate that a larger size of femoral component should be selected in order that stability of the patello-femoral joint is not compromised. In order to provide an indication of the suitability of the component size using a scale from, for example "−2" to "+2" when the thickness of the anterior flange of the femoral component varies across the size range, it will generally be necessary for the instrument to include the ramp feature as discussed above, where the ramp is configured to take account of the range of thickness of the anterior flange, and the length from end of the anterior flange the point along its length at which the thickness of the flange is at a maximum. When the thickness of the anterior flange does not vary across the size range, the scale on the sulcus arm can provide an indication of the suitability of the component size using a scale from, for example "−2" to "+2" without the ramp feature.

It is also possible to use the scale on the sulcus arm to provide an indication of the absolute distance (for example in millimeters) between the tip 24 of the sulcus arm and the anterior arm. From this, it is possible to calculate the distance between the tip and the posterior condyles, using the size information obtained in the first measurement step described above. This can be used to identify an appropriate size of femoral implant component having regard to the distance between the posterior condyles and the sulcus.

Figure 4:
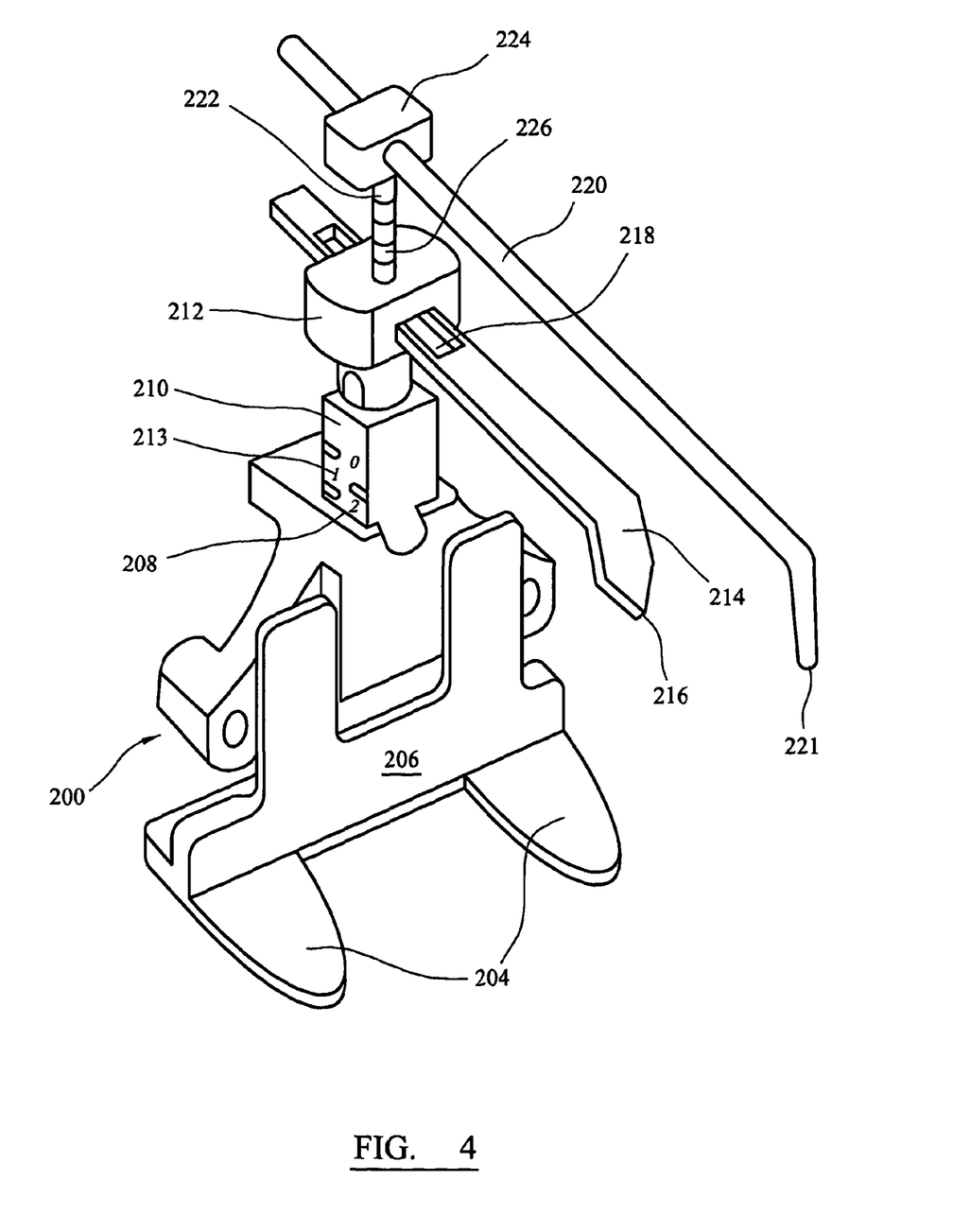
FIG. 4 is an isometric view of another embodiment of a femoral sizing instrument for use in a knee joint replacement procedure.

FIG. 4 shows an instrument 200 for measuring a femur in a knee joint replacement procedure. It comprises a housing with posterior plates 204 and a distal plate 206. The housing has a bore 208 formed in it in which a primary connector leg 210 can be received and can slide, in a direction which is generally parallel to the distal plate 206. The position of the primary connector leg can be clamped against sliding relative to the housing by means of a threaded screw which can be screwed into a threaded hole in the housing so that the end of the screw acts against the connector leg. Locking screws of this type are known.

The connector leg has a primary hub 212 its upper end with a bore extending through it. The connector leg has a scale 213 marked on it.

The instrument includes a sulcus arm 214. The sulcus arm is sized to be a sliding fit in the bore in the hub 212 on the connector leg. The sulcus arm 214 has a tip 216. It has a slot 218 formed in it extending along part of its length.

The primary hub 212 and the primary connector arm 210 have a bore extending at least into the upper part of the connector arm.

The instrument includes a cortex arm 220 having a tip 221. The cortex arm is mounted on a secondary connector arm 222 which is a sliding fit in the bore in the primary hub 212 and the primary connector arm 210. The cortex arm is a sliding fit in a bore in a secondary hub 224 which is provided on the secondary connector arm. A scale 226 is provided on the secondary connector arm.

The height of the sulcus arm 214 relative to the posterior plates 204 can be adjusted by sliding the primary connector arm 210 relative to the housing.

The height of the cortex arm 220 relative to the sulcus arm and to the posterior plates can be adjusted by sliding the secondary connector arm 222 relative to the primary connector arm 210.

Each of the sulcus arm and the connector arm can be slid in its respective hub relative to its connector arm so that the effective length of the arm is suitable to position the tip of the arm on the sulcus or on the anterior cortex. Each of the arms can be restrained selectively against sliding relative to its hub by means of, for example, a locking screw or a series of indents on the arm operating in conjunction with a resiliently deformable tooth.

The distance from the posterior condyle to the sulcus can be determined by inspecting the scale on the primary connector arm. The distance between the sulcus and the anterior cortex, measured in a direction which is generally perpendicular to the axis of the femur, can be determined by inspecting the scale on the secondary connector arm. The distance from the posterior condyle to the anterior cortex can be determined by inspecting the scales on the primary and secondary connector arms. The distance information derived in this way can be used to select a size of femoral component of a kneed joint prosthesis according to the measured size of the patient's femur.

The invention claimed is:

1. A femoral sizing instrument for use in a knee joint replacement procedure, wherein the knee joint replacement procedure includes replacing the distal femur, the distal femur having an anterior cortex, medial and lateral condyles with distal and posterior surfaces and a sulcus, which comprises:
   a housing having a first location face for contacting the distal surface of the femur, and a second location face for contacting the posterior surface of at least one of the medial and lateral femoral condyles;
   a cortex arm attached to the housing, the cortex arm having a first portion extending outwardly from the housing in a first direction and a second portion having a tip for engaging the anterior cortex of the femur, the second portion extending from the first portion in a second direction different from the first direction;
   a sulcus arm having a tip for engaging the sulcus, wherein the sulcus arm extends from the first portion of the cortex arm in a direction different from the first direction, the cortex arm is adjustable relative to the housing to alter the distance between the tip of the second portion of the cortex arm and the housing, the sulcus arm is adjustable relative to the first portion of the cortex arm to alter the distance between the tip of the sulcus arm and the housing and each of the cortex and sulcus arms is adjustable relative to the housing to alter the distance between each respective tip and the posterior surfaces of the medial and lateral condyles; and at least one scale for indicating the positions of the respective tips of the cortex and sulcus arms relative to the housing, wherein the scale is associated with at least one of the housing, the cortex arm and the sulcus arm;

wherein the first portion of the cortex arm has a slot receiving part of the sulcus arm therein, so that the sulcus arm is capable of slide along the first portion of the cortex arm to selectively adjust the distance between the tips of the cortex and sulcus arms;

wherein the cortex arm includes indicia alongside the slot; and wherein the instrument further comprises a locking device to selectively lock the sulcus arm against movement along the slot of the cortex arm.

2. The instrument of claim 1, wherein the sulcus arm is adjustable relative to the first portion of the cortex arm to alter the distance between the tip of the sulcus arm and the posterior surfaces of the medial and lateral condyles without altering the distance between the tip of the cortex arm and the posterior surfaces of the medial and lateral condyles.

3. The instrument of claim 2, wherein the sulcus arm moves with the cortex arm when the cortex arm is adjusted to vary the distance between the posterior surfaces of the medial and lateral condyles and the tip of the sulcus arm.

4. The instrument of claim 1, wherein the sulcus arm has an adjustable length measured between the first portion of the cortex arm and the tip of the sulcus arm.

5. The instrument of claim 1, wherein the cortex arm has an adjustable length measured between the housing and the tip of the cortex arm.

6. The instrument of claim 1, wherein the housing comprises a connector leg that extends between the housing and the cortex arm, the connector leg having length, and wherein the connector leg is movable relative to the housing so that the length of the connector leg, measured from the housing to the cortex arm is adjustable.

7. The instrument of claim 6, further comprising a leg locking device that locks the position of the connector leg relative to the housing.

8. The instrument of claim 6, wherein the cortex arm is slidable relative to the connector leg, and includes an arm locking device that locks the arm against sliding relative to the connector leg.

* * * * *